Figure 1:
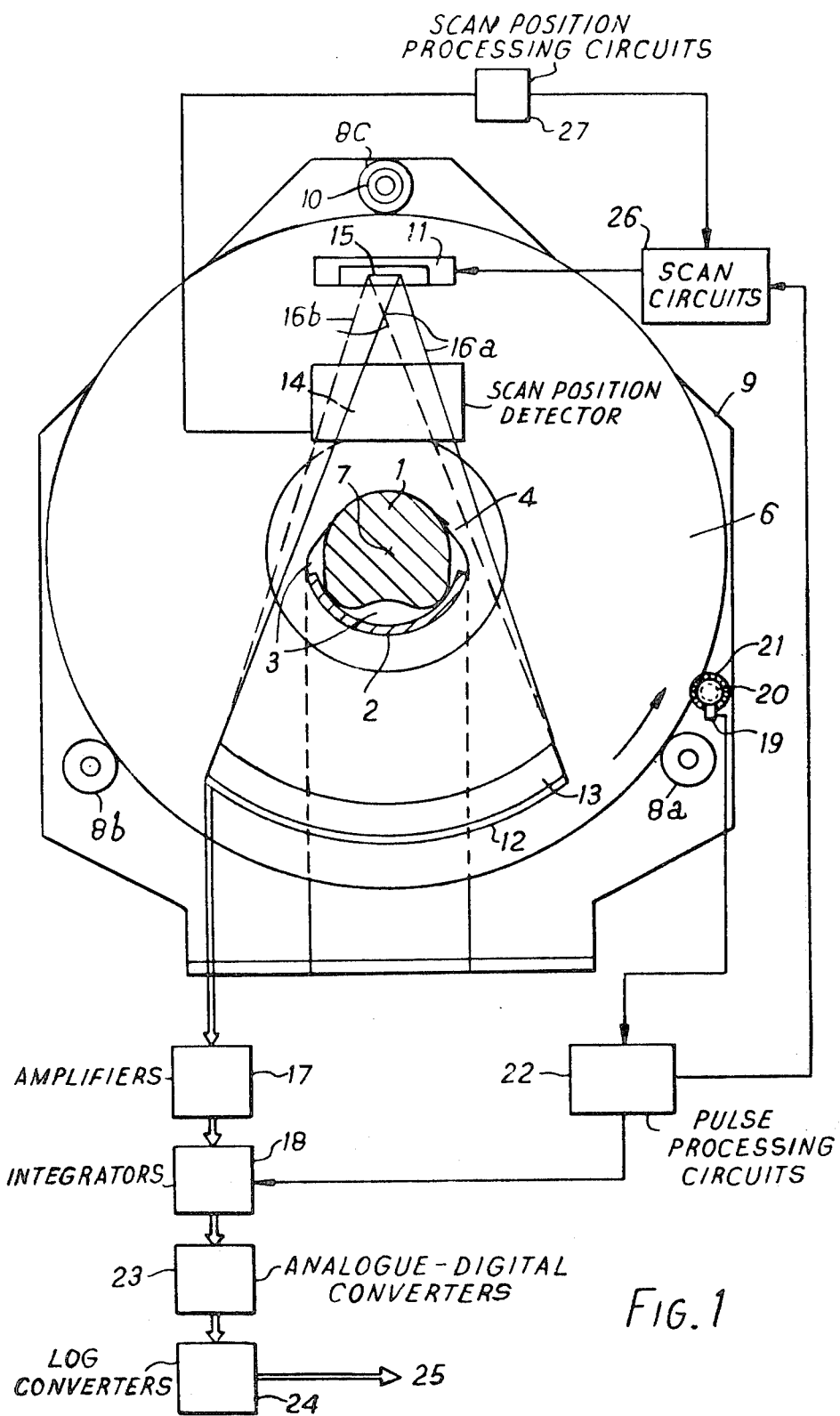

United States Patent [19]

Fairbairn

[11] 4,211,925
[45] Jul. 8, 1980

[54] CT SCANNER WITH ANODE SCAN MONITOR

[75] Inventor: Ian A. Fairbairn, Maidenhead, England

[73] Assignee: E M I Limited, Middlesex, England

[21] Appl. No.: 897,787

[22] Filed: Apr. 19, 1978

[30] Foreign Application Priority Data

Apr. 28, 1977 [GB] United Kingdom ............... 17744/77

[51] Int. Cl.$^2$ .............................................. A61B 6/00
[52] U.S. Cl. ............................. 250/445 T; 250/355
[58] Field of Search ............. 250/503, 355, 397, 398, 250/445 T

[56] References Cited

U.S. PATENT DOCUMENTS

| | | | |
|---|---|---|---|
| 2,946,892 | 7/1960 | Bas-Taymay | 250/355 |
| 3,778,614 | 12/1973 | Hounsfield | 250/445 T |
| 3,866,047 | 2/1975 | Hounsfield | 250/445 T |
| 3,924,129 | 12/1975 | Le May | 250/445 T |
| 3,946,234 | 3/1976 | Hounsfield | 250/445 T |
| 4,010,370 | 3/1977 | Le May | 250/445 T |
| 4,035,647 | 7/1977 | Hounsfield et al. | 250/445 T |
| 4,123,659 | 10/1978 | Oliver | 250/403 |

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In a variant of the type of radiographic apparatus known as CT scanners a scanning X-ray tube is used to provide a planar fan-shaped distribution and to scan the distribution in its plane. Means are also provided to rotate the system about an axis perpendicular to the plane. In order to properly relate operation of the system, it is desirable to monitor the progress of the tube scan. This invention disposes a detector into the radiation and a pair of gratings acting together to modulate the radiation, incident on the detector, in relation to the scan position. The detector output is processed to give pulses which can be used to regulate the tube scan.

6 Claims, 6 Drawing Figures

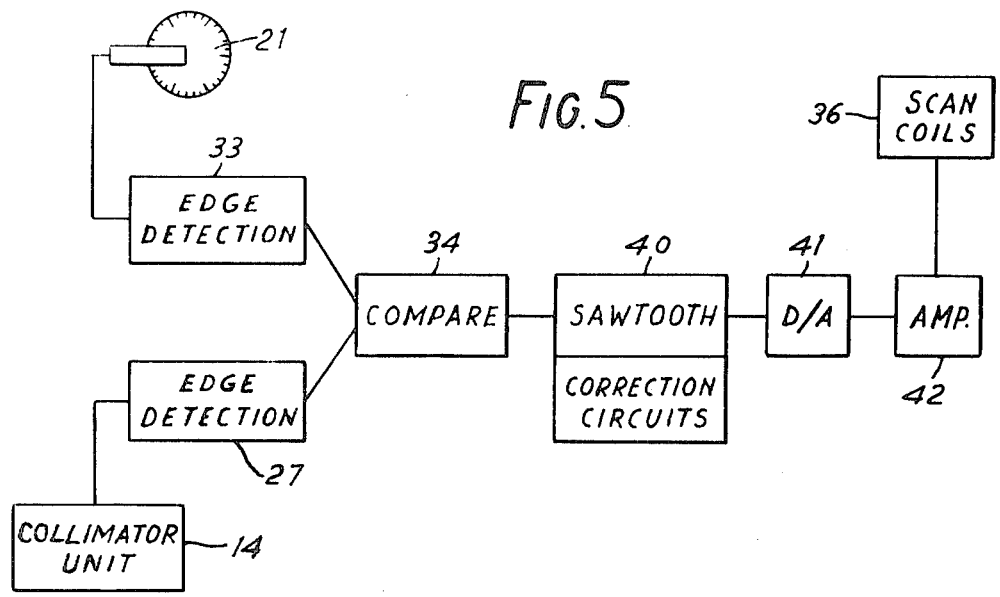
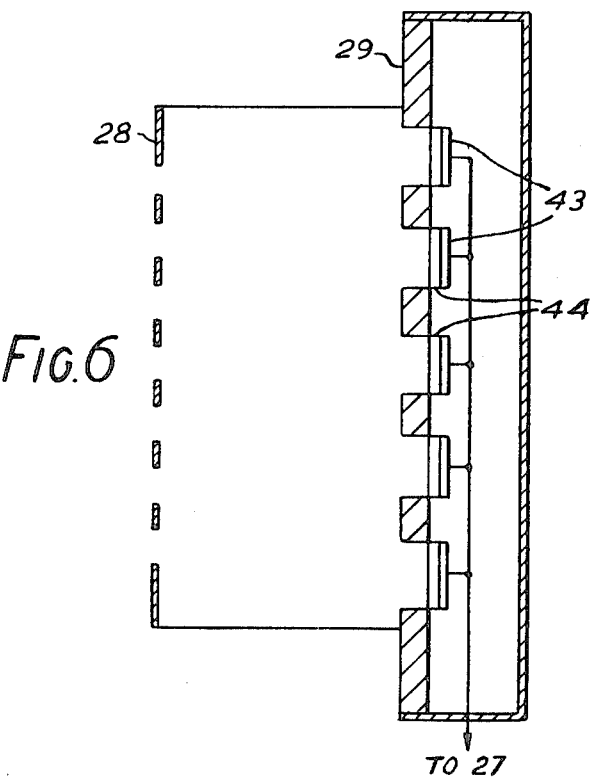

CT SCANNER WITH ANODE SCAN MONITOR

This invention relates to a method of and apparatus for constructing a representation of the variation of absorption with position across a planar slice of a body with respect to penetrating radiation such a X-radiation.

A method of and apparatus for constructing such a representation is described in U.S. Pat. No. 3,778,614. According to one example given in that specification, a scanning movement is imparted to a suitable source of radiation and a detector to provide a measure of the absorption suffered by each of a plurality of beams of radiation passing through the body in the plane of the slice. A technique for processing the absorption measurement is also disclosed in the said specification.

Scanning techniques capable of obtaining the desired data more rapidly are disclosed in U.S. Pat. Nos. 3,946,234 and 4,035,647. An alternative version of the processing method which involves a form of convolution has also been described in U.S. Pat. No. 3,924,129.

Further scanning techniques, which are developments of that disclosed in the said specification No. 4,035,647 have been described in U.S. Pat. No. 4,010,370 and United States application No. 733,941 now Patent No. 4,115,698. In the arrangements described therein a source of a fan shaped spread of radiation, lying in a substantially planar region of examination is rotated about an axis substantially perpendicular to the fan to direct the radiation through the region of examination from many directions. A plurality of detectors are arranged to measure the absorption of the radiation along individual beam paths in the fan at different angular positions thereof. In order to irradiate the region at a sufficient number or orientations, additional motions may be imposed on the fan of radiation. In the example described in the said Patent No. 4,010,370 and application No. 733,941 there are used X-ray sources which incorporate an elongated anode providing the fan shaped beam from a substantially point source at which an electron beam strikes the anode. By scanning the electron beam along the anode the point of origin of the X-rays is also scanned so that a lateral motion of the fan is superimposed on the orbital motion. Desired orientations of the fan in relation to the body can thus be provided by a suitable relationship between the said two motions.

In United States application No. 799,712 now U.S. Pat. No. 4,123,659 there is described one arrangement for suitably relating the two motions. That arrangement comprises a collimator block inserted in the X-ray path before a scintillator and photomultiplier so that X-rays fall on the scintillator with a periodic intensity related to the scan progress. The photomultiplier output is then processed to yeild timing pulses for the X-ray source scan.

It is an object of this invention to provide an alternative arrangement for such timing.

According to the invention there is provided a radiographic apparatus for examining a slice of the body of a patient, including a source of a substantially planar fan-shaped distribution of radiation originating from an anode included in the source, means for scanning the origin of the radiation in relation to the anode and a scan position indicator including means for detecting the intensity of the radiation and at least two gratings, disposed to shield the means for detecting, co-operating to modulate the intensity of the radiation incident on the means for detecting in a manner related to the position of said origin.

Figure 2:
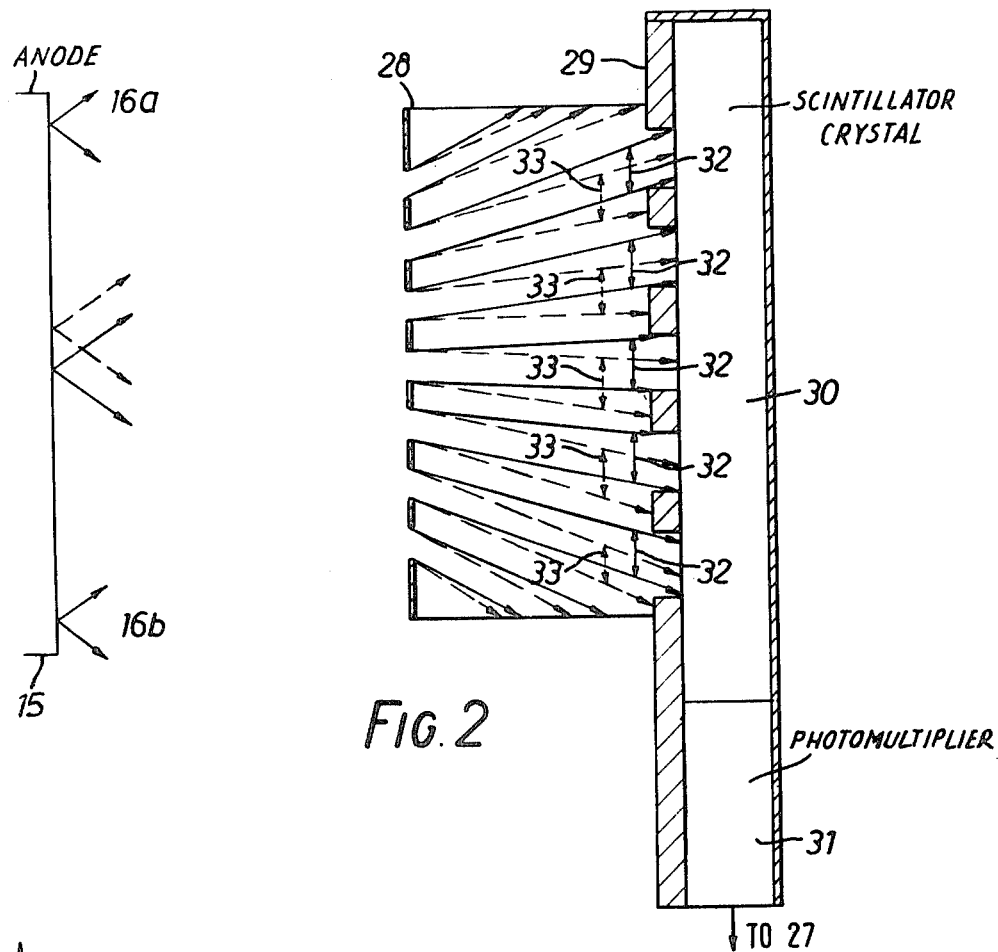
Figure 3:
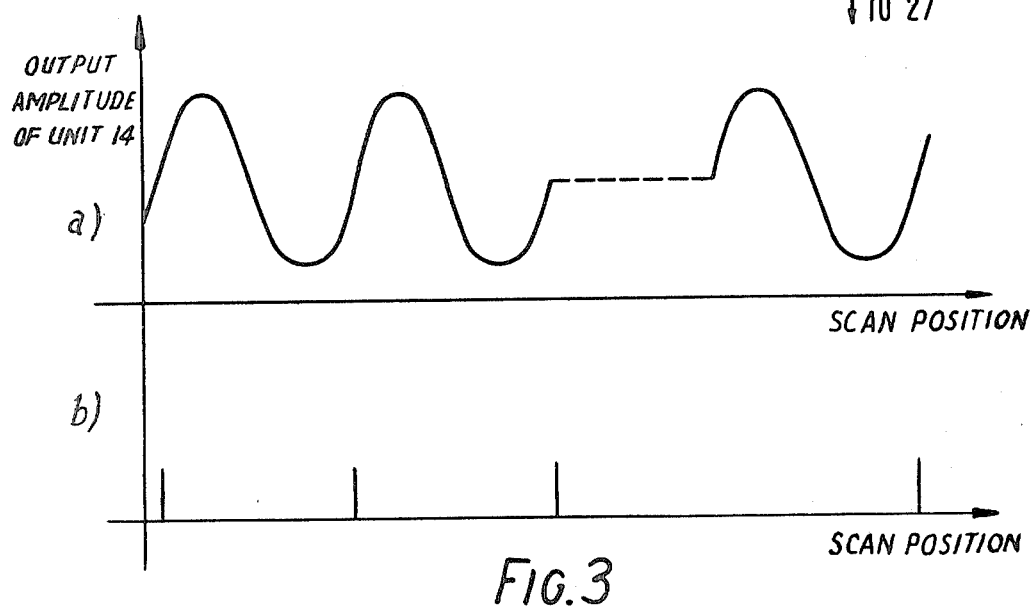
Figure 4:
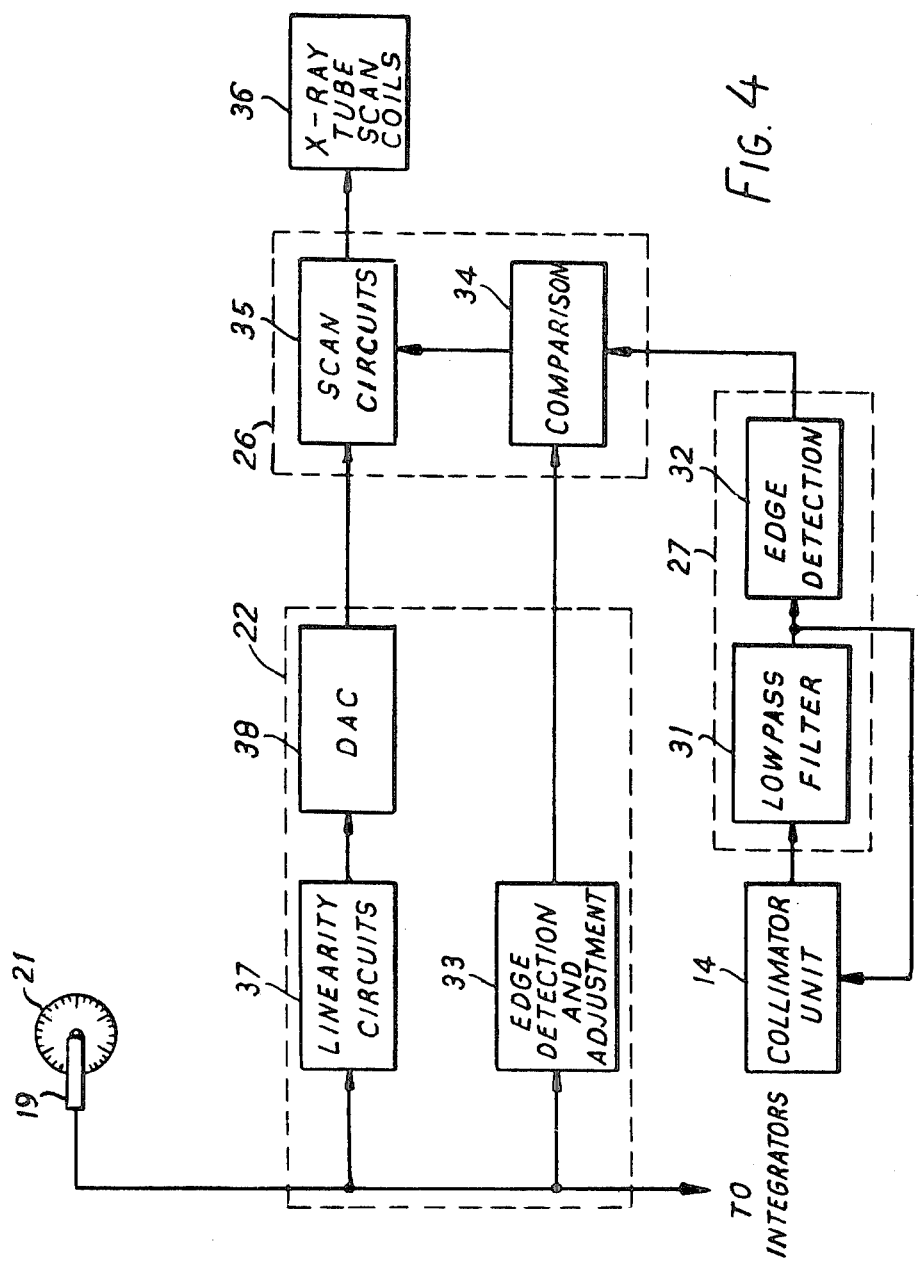

In order that the invention may be clearly understood and readily carried into effect an example thereof will now be described with reference to the accompanying drawings of which, FIG. 1 shows an apparatus incorporating the invention, FIG. 2 shows a collimator detector arrangement for implementing the invention, FIG. 3 illustrates the form of the output of the arrangement of FIG. 2, FIG. 4 is a block diagrammatic circuit for processing the control signals for the apparatus of FIG. 1, FIG. 5 is a block diagram of an alternative circuit for processing the control signals and FIG. 6 shows an alternative collimator detector arrangement utilising photodiodes.

Referring to FIG. 1, there is shown therein apparatus substantially the same as that described in the said applications No. 733,941 and No. 799,712 now U.S. Pat. Nos. 4,115,698 and 4,123,659 respectively. A body 1 to be examined, shown in transverse section, is supported on a suitably shaped bed 2 also shown in transverse section. A material 3, having an absorption to the radiation similar to that of body tissue, is positioned between the body 1 and the bed 2, to substantially exclude air from gaps therebetween, and is extended partly about the body, to provide an approximately circular crosssection to the radiation. The body is retained firmly in the desired position by means such as a restraining strap 4.

The bed 2 and the body 1 are inserted into an aperture 5 in a rotatable member 6 so that a desired part of the body is centred in the aperture. The rotatable member 6 is arranged to rotate about an axis 7, in this example longitudinal to the body and perpendicular to the paper, central to the aperture 5. For that purpose it is supported by three gear wheels 8a, b, c, which engage with gear teeth, not shown, cut into the periphery of member 6. The gear wheels 8 are journalled in the main frame 9 of the apparatus. Gear wheel 8c is driven by a motor 10, also mounted on the main frame 9, to provide the necessary rotation.

The rotatable member 6 also carries a source 11 of X-rays, a bank of detectors 12 and associated collimators 13. The detectors, which in a typical embodiment number 300–400 can be of any suitable type, for example scintillation crystals with associated photomultipliers or photodiodes. A scan position detector unit 14, which will be described in greater detail hereinafter, is also mounted on the main frame so as to be irradiated by the X-rays. In order to receive X-rays without shielding detectors 12, the unit 14 is displaced perpendicularly to the plane of examination i.e. perpendicular to the plane of the paper. The fan of X-rays is arranged to be at least of sufficient extent in that direction to irradiate this unit.

The source 11, which includes an elongated target-/anode 15 as mentioned hereinbefore, provides a fan shaped spread 16 of X-rays from an area, which may be a point or a larger area such as a line, at which an electron beam is incident thereon. The electron beam can be scanned along the elongated anode to scan the X-rays correspondingly from the position 16a to the position 16b. This gives the effect of an extended source of X-rays although all of the radiation is not produced at one time. In this example the corresponding scan of the area, which is the origin of the X-rays, along target 15 is of the order of five cm. although it may be more or less if desired. The collimators have longitudinal axes which intersect in the region of the centre of anode 15.

Correspondingly the X-ray source 11 is placed of the order of 50 cm. from the central axis 7 with the detectors 12 being placed a further 50 cm. on the opposite side of axis 7 so as to intercept the radiation of fan 16 for any position of the origin of the X-rays in its lateral scan along target 15. If desired, however, the distances from source to axis 7 and detectors to axis 7 may be unequal. It should be understood that collimators 13 are of dimensions and construction which allow proper interception of the directly transmitted radiation while preventing the reception of scattered radiation to the greatest degree practically possible. Unit 14 may be placed closer to the source than shown provided it can intercept part of the radiation at all points of the scan without obscuring detectors 12.

The arrangement is such that the origin of the X-rays is scanned steadily along target 13 taking the fan of X-rays from 16a to 16b and is rapidly returned to the starting point before repeating the scan. Simultaneously the rotary member 6 and the equipment mounted thereon are subject to a required rotation. During this time each detector of array 12 is providing an output indicative of the intensity of radiation incident thereon. These outputs are amplified in amplifiers 17 and then applied to integrators 18. There the outputs are integrated over periods chosen such that each integrated output is related to the intensity of radiation transmitted along a beam path, of dimensions determined by the rotational motion and source point linear motion in that period. Since these motions are related in a manner chosen to achieve desired beam paths for a particular embodiment, say that of application No. 733,941, now Patent No. 4,115,698 the required periods of integration are also related to these motions. For this purpose the integrators are, in this example set and reset by pulses of period related to the orbital motion. These pulses are provided by a light source and photocell unit 19 mounted on main frame 9. Journalled in main frame 9 is a further gear wheel 20 engaging the teeth cut in the periphery of member 6. Carried on wheel 20 is a circular graticule 21 which thus rotates with member 6. The graticule 21 comprises opaque lines on a transparent substrate so that these lines interrupt a light path between the said light source and photocell to give pulses indicating the progress of the rotary motion. The pulses are applied to integrators 18 via a unit 22 which will be discussed hereinafter.

In this example the timing of the pulses is such that there are twenty four integration periods in the time of one lateral scan of the X-ray fan 16 and 16a to 16b. Thus each detector measures radiation in effect along twenty four narrow beam paths joining that detector with twenty four equally spaced positions along target 13. The actual shape of the paths through the body will also be determined, as mentioned hereinbefore, by the simultaneous orbital motion. Signals representing the intensity of radiation received along those paths are converted to digital form in converters 23 and to logarithmic form in converters 24 for output at 25 for further processing. It will be understood that one amplifier 17, integrator 18, A/D converter 23 and log converter 24 is provided for every detector, all operated in sychronism. The processing is effective to sort the signals into suitable form, for example into sets representing absorption along sets of parallel paths as explained in application No. 733,941 now Patent No. 4,115,698, for processing by a suitable method such as that described in U.S. Pat. No. 3,924,129 to provide the desired representation. The circuits referred to are of well known construction.

As mentioned hereinbefore it is desired to maintain the scanning of X-ray source 11 in a required relationship with the continuous rotary motion. For this purpose scan circuits 26, controlling the scanning of the incident electron beam along anode 15, are provided with the pulses from light source and photocell unit 19 via graticule pulse processing circuits 22. It is however also desirable to monitor the actual lateral motion of the X-rays to ensure that the relationship is properly achieved. An output for this purpose is provided by unit 14, via processing circuit 27 also to scan circuits 26.

The arrangement of the scan position detector unit 14 is shown in greater detail in FIG. 2. The fan of X-rays is shown at two positions between the scan limits 16a and 16b. Disposed slightly out of the plane of examination, unit 14 comprises: a first lead grating 28 with openings at a first pitch; a second lead grating 29 with openings at a second pitch; a scintillator crystal 30 shielded by the grating 29, and disposed to receive radiation which has passed through the openings in both gratings; and a photomultiplier or similar photo sensitive device 31, disposed to detect light emitted by crystal 30 in response to incident radiation.

The two gratings are preferably placed at distances, from the locus of the source spot, proportional to their respective pitches. They co-operate such that, for some source spot positions, for example that for which radiation is indicated by solid lines, beams 32, formed by the first grating, are admitted by the second grating to crystal 30, whereas for other positions, for example that for which radiation is indicated by broken lines, beams 33, formed by the first grating, are at least partly excluded from crystal 30 by the second grating.

Clearly, as the origin of the radiation is scanned across anode 15, the beams, defined by grating 28 are swept across grating 29. The proportion of radiation admitted to crystal 30 varies periodically and the output of photomultiplier 31 is similarly periodic. In practice the output approximates to a sinusoid as shown in FIG. 3(a).

It will be understood that, if this output is to be used for timing procedures, a sinusoid is not a convenient form. It is therefore, after filtering to reduce noise, applied to an edge detection circuit. Such circuits maybe devised to provide a pulse indicating the detection of a leading edge, as in FIG. 3b, or a trailing edge. Alternatively a more complex circuit may be provided to detect the leading and trailing edges and to provide pulses, with a suitable delay, indicative of the relative timing of the peaks midway between the two edges. Such pulses would more closely indicate the presence of the centre of the X-ray origin. The frequency of the pulses is dependent on the spacings of the apertures of the two gratings. These would normally be much smaller and more closely spaced than those in FIG. 2 which is simplified for the purposes of illustration.

As can be seen from FIG. 2 the radiation will irradiate progressively less openings of grating 29 at each end of the scan. However that reduction of intensity is superimposed on the sinusoid of FIG. 3a and would not disturb the pulses to be derived. It can be avoided by increasing the lateral extent of both graticules.

A block diagram of the timing circuits is shown in FIG. 4. The output of the photomultiplier in unit 14 is processed as described by a low pass filter 31 and edge detection circuit 32, together constituting circuits 27, to give pulses indicative of the progress of the X-ray scan. The overall amplitude of the output, from low pass filter 31 may be fed back to the photomultiplier as a gain control for stabilisation purposes.

The photocell unit 19 associated with graticule 21 provides pulses indicating the integration intervals referred to hereinbefore and pulses indicating the correct times, for a desired scan relationship, of the pulses, such as those of FIG. 3b, which represent a chosen characteristic of the output of unit 14. These two sets of pulses may be identical, if the relationship is suitable, or may be independent, but of related timing. In the latter case they can be provided by two photocells detecting lines of different graticules on wheel 20.

The X-ray timing pulses are provided to edge detection circuits 33 which provide pulses of suitable form for comparison and also allow fine adjustment of their relative timing for use in initially setting up the apparatus. The pulses are then compared in circuits 34 with the actual scan pulses derived from unit 14. Any errors of timing between the two are applied to X-ray scan circuits 35 which control the X-ray tube scanning coils, indicated generally at 36, to correct the X-ray scan timing. Circuits 34 and 35 constitute the circuits 26 referred to hereinbefore.

The initial scan sawtooth, prior to adjustment in circuits 35, may be preset. However in a preferred embodiment the sawtooth is derived from the pulses provided by photocell unit 19. These are used by linearity circuits 37, which may be digital, to provide a sawtooth which is approximately related to the rotation rate, scan circuits 35 then provide a fine adjustment. If circuits 37 are digital their output is in the form of a pulse train which is applied to a digital to analogue converter (DAC) 38 to give the actual sawtooth.

It will be understood that other circuits may be devised to control the X-ray scan from the output of unit 14. These may be arranged to obtain timing from any repeating characteristic of the waveform of FIG. 3a or a similar waveform resulting from an alternative form of unit 14. For example FIG. 5 shows one alternative circuit to that of FIG. 4. The circuit of FIG. 7 takes the pulses derived from the collimator unit 14 by edge detector 27 and compares them directly in a unit 34 with the timing signals from graticule 21.

Signals representing the timing differences resulting from the comparison are applied to a unit 40 which provides an adjusted sawtooth output. This sawtooth is continuously adjusted, in practice over discrete small sections, to provide a sawtooth tending to cause the scan to conform to the timing signals. The sawtooth is in practice produced in digital form, in which case it must be converted into analogue form in a converter 41. It is then amplified in a drive amplifier 42 and applied to the scan coils 36.

Furthermore the single detector providing outputs for different scan positions, by receiving radiation from all openings of grating 29 may be replaced by a plurality of individual detectors, such as photodiodes perhaps co-operating with individual scintillators, spaced across the X-ray scan. Such an arrangement is shown in FIG. 6, in which photodiodes and scintillators are indicated by references 43 or 44 respectively.

What I claim is:

1. A radiographic apparatus for examining a slice of the body of a patient, including a source of a substantially planar fan-shaped distribution of radiation originating from an anode included in the source, means for scanning the origin of the radiation in relation to the anode and a scan position indicator including means for detecting the intensity of the radiation and at least two gratings, disposed to shield the means for detecting, co-operating to modulate the intensity of the radiation incident on the means for detecting in a manner related to the position of said origin.

2. An apparatus according to claim 1 in which the two gratings are of different pitches and the ratio of the pitches is substantially the same as the ratio of the distances of the gratings from the locus of the scanned origin of the radiation.

3. An apparatus according to claim 1 in which the means for detecting the intensity of the radiation includes a scintillator cooperating with at least one photomultiplier.

4. An apparatus according to claim 1 in which the means for detecting the intensity of the radiation includes a plurality of photodiodes.

5. An apparatus according to claim 4 in which one photodiode is provided for each of a plurality of apertures of one of the gratings.

6. An apparatus according to claim 4 in which the plurality of photodiodes co-operate with a plurality of scintillators to detect the intensity of the radiation.

* * * * *